United States Patent
Zhang

(10) Patent No.: US 10,350,230 B2
(45) Date of Patent: Jul. 16, 2019

(54) USE OF ALBIFLORIN OR PHARMACEUTICALLY ACCEPTABLE SALT FOR PREVENTION AND/OR TREATMENT OF IRRITABLE BOWEL SYNDROME

(71) Applicant: Zuoguang Zhang, Dongcheng District (CN)

(72) Inventor: Zuoguang Zhang, Dongcheng District (CN)

( * ) Notice: Subject to any disclaimer, the term of this patent is extended or adjusted under 35 U.S.C. 154(b) by 0 days.

(21) Appl. No.: 15/554,176

(22) PCT Filed: Apr. 27, 2015

(86) PCT No.: PCT/CN2015/077489
§ 371 (c)(1),
(2) Date: Aug. 28, 2017

(87) PCT Pub. No.: WO2016/134563
PCT Pub. Date: Sep. 1, 2016

(65) Prior Publication Data
US 2018/0028550 A1  Feb. 1, 2018

(30) Foreign Application Priority Data

Feb. 26, 2015  (CN) .......................... 2015 1 0087514

(51) Int. Cl.
*A61K 31/7048* (2006.01)
*A61K 31/365* (2006.01)

(52) U.S. Cl.
CPC ........ *A61K 31/7048* (2013.01); *A61K 31/365* (2013.01)

(58) Field of Classification Search
CPC .................................................. A61K 31/7048
See application file for complete search history.

(56) References Cited

U.S. PATENT DOCUMENTS

2002/0068097 A1  6/2002  Basu
2013/0316966 A1*  11/2013  Zhang ................ A61K 31/7048
514/27

FOREIGN PATENT DOCUMENTS

| CN | 1895384 A | 1/2007 |
| CN | 101623366 | 1/2010 |
| CN | 103585289 | 2/2014 |
| CN | 103735685 | 4/2014 |
| EP | 2644198 A1 | 10/2013 |
| WO | WO-2005074952 A1 | 8/2005 |
| WO | WO-2016134563 | 9/2016 |

OTHER PUBLICATIONS

English machine translation of CN103735685A, Google Patents, https://patents.google.com/patent/CN103735685A, accessed online on Jun. 21, 2018. (Year: 2018).*
Definition of prevent, Oxford English Dictionary Online, http://dictionary.oed.com/, accessed online Mar. 27, 2010, especially definition 9a. at p. 2. (Year: 2010).*
He et al., Front. Pharmacol., 2011, 2, article 10, 5 pages. (Year: 2011).*
Li et al., Pharm Clin Chin Mater Med (Chin), 2011, 2(6), p. 38-41, English abstract only. (Year: 2011).*
Wang et al., Pharm. Biol., 2014, 52(9), p. 1189-1195. (Year: 2014).*
Lee, S., Chromatographic analysis of a herbal formulation for the treatment of C-IBS, Diss., U. Western Sydney, 2009. (Year: 2009).*
"International Application No. PCT/CN2015/077489, International Search Report and Written Opinion dated Nov. 20, 2015", (dated Nov. 20, 2015), 12 pgs.
"European Application No. 15883001, Extended European Search Report dated Aug. 8, 2018", (dated Aug. 8, 2018), 8 pgs.
Choung, Myoung Gun, et al., "Isolation and Determination of Paeoniflorin and Albiflorin in Korean Peony (*Paeonia lactiflora pall*) Root", Korean J. medicinal Crop Sci., 5(4), (1997), 249-254.

* cited by examiner

*Primary Examiner* — Jonathan S Lau
(74) *Attorney, Agent, or Firm* — Schwegman Lundberg & Woessner, P.A.

(57) ABSTRACT

Disclosed is a use of albiflorin or a pharmaceutically acceptable salt for the prevention and/or treatment of irritable bowel syndrome. The experimental results demonstrate that the prevention, remission and/or treatment of irritable bowel syndrome with albiflorin or a pharmaceutically acceptable salt has significant effects and few side effects. This is a preparation derived from a natural plant for the safe, effective and multi-targeted prevention, remission and/or treatment of irritable bowel syndrome.

7 Claims, 1 Drawing Sheet

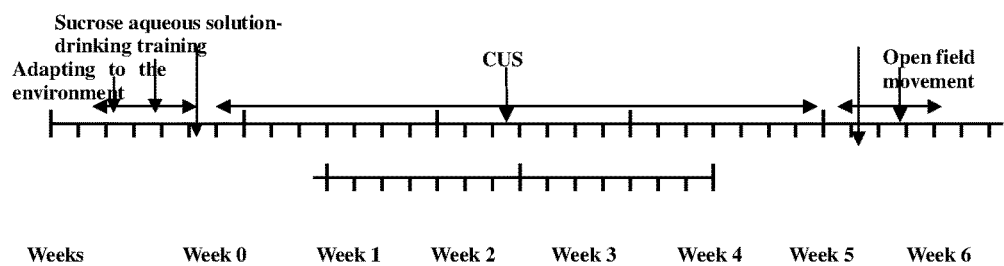

USE OF ALBIFLORIN OR PHARMACEUTICALLY ACCEPTABLE SALT FOR PREVENTION AND/OR TREATMENT OF IRRITABLE BOWEL SYNDROME

PRIORITY CLAIM TO RELATED APPLICATIONS

This application is a U.S. national stage application filed under 35 U.S.C. § 371 from International Application Serial No. PCT/CN2015/077489, which was filed 27 Apr. 2015, and published as WO2016/134563 on 1 Sep. 2016, and which claims priority to Chinese Application No. 201510087514.X, filed 26 Feb. 2015, which applications and publication are incorporated by reference as if reproduced herein and made a part hereof in their entirety, and the benefit of priority of each of which is claimed herein.

FIELD OF THE INVENTION

The present invention relates to a novel use of albiflorin or a pharmaceutically acceptable salt thereof in the preparation of a medicament or a health-care food for preventing, relieving and/or treating irritable bowel syndrome.

BACKGROUND OF THE INVENTION

Irritable bowel syndrome (IBS) is one of the most common gastrointestinal disorders in clinical practice. In recent years, it has been recognized in the art as a gut brain disease with specific pathological and psychological factors. It is a set of symptoms including abdominal pain, abdominal distension, bowel evacuation habit changes and stool abnormalities, mucous stool and the like. According to clinical manifestation, IBS can be generally divided into four types, i.e. diarrhea type, constipation type, alternating diarrhea and constipation type and abdominal pain type, in which the diarrhea type accounts for about ⅔. Epidemiological investigation shows that, 10% to 20% of population around the world have suffered from IBS symptoms. In Europe and the United States, this disease accounts for more than 50% of the gastrointestinal outpatient. The incidence of IBS in Chinese is 7.01%, in which a significant number of patients are associated with depression, anxiety and sleep disorders. Since the patients often complain of a gastrointestinal symptom as the main symptom, they are usually treated and modulated by doctors as gastrointestinal motility abnormalities, therefore, the efficacy is poor.

The occurrence of IBS is closely related to mental, psychological, emotional factors and environmental stress. IBS patients often suffer from nervousness, emotional irritability, unease, anxiety and depression. The study shows that, 50% to 90% of IBS patients have mental disorders such as anxiety and depression; more than 50% of patients have sleep disorders such as ease to wake up and morning fatigue. The increase of glucocorticoid induced by stress (HPA axis hyperactivity) can directly promote the excitement of brain amygdala, which is the main center for regulating the body and visceral stress, the excessive and continued increase of glucocorticoid can induce changes in colorectal tension sensitivity. Therefore, IBS could be appropriately relieved and treated through reverse regulation of the hyperactive HPA axis and inhibition of excessive secretion of glucocorticoids.

In addition to mental and environmental stress factors, IBS could also be induced by change of gastrointestinal motility, gastrointestinal disorder and gastrointestinal infection, intolerance to one or more foods, allergy and abnormality of gastrointestinal endocrine hormone activity, for example content increase of motilin (MTL) and sigmoid colon mucosal vasoactive intestinal peptide (VIP).

Since IBS is a complex multi-target integrated disease of multiple mental-physiological factors, there still lacks an efficient drug for treating irritable bowel syndrome in modern medicine at present ("*Research Ideas and Methods on Efficacy of Traditional Chinese Medicine*", P449). Symptomatic treatment is usually used in clinical practice. The drugs commonly used include antispasmodic drug, gastrointestinal-kinetic promoter or inhibitor, antiflatulent, laxative, antidiarrheal drug, drug for regulating visceral sensitivity and the like. The antidepressant and antianxietic drugs can not only improve the mental state of patient, but also regulate the gastrointestinal function of patient. They are also used by doctors as drugs for treating IBS in combination with other types of drugs, for example, calcium ion antagonist pinaverium bromide is combined with fluoxetine in clinical practice. Although the combined administration can increase efficacy to a certain extent, the side effects are also superimposed, which seriously affect the life quality of the user. The combined administration also increases the cost of treatment, and increases the economic burden of patients and society.

The ideal drug for treating IBS should meet the following requirements:

1. it has multiple functions of antidepressant, antianxiety, antiallergic, anti-inflammatory, antidiarrheal, analgesic, regulating gastrointestinal function and reducing visceral sensitivity and improving sleep;

2. it has few side effects, is safe, and can be administered to the patient over a long term for conditioning treatment;

3. its quality is controllable, its administration is convenient, its cost is moderate, which will not give the patient an excessive economic burden.

Traditional Chinese Medicine concentrates on regulating the emotion of patient during the treatment of IBS, for example, the famous "pain-diarrhea formulation" (described in "*Jing Yue's Complete Works*") has good efficacy in the treatment of diarrhea-predominant irritable bowel syndrome. However, the formulation comprises a large number of herbal medicines, which are used in a large amount, and the preparation method is rather primitive. Therefore, the quality of the formulation is not controllable, and the administration is not convenient.

The inventor learns from the Traditional Chinese Medicine formulation, which treats IBS by soothing liver to relieve depression and improving spleen function to calm the nerves, and uses modern pharmacology as guidance. Based on the previous research on antidepressant and drug for improving sleep, the inventor successfully uses albiflorin or a pharmaceutically acceptable salt thereof for treating irritable bowel syndrome by means of computer system targeting research via repeated validation of efficacy.

Albiflorin or a pharmaceutically acceptable salt thereof of the present invention compensates for the defect and deficiency of existing drugs for treating IBS. It is an ideal natural product for preventing and treating IBS, because it starts from multiple targets, and has multiple functions of antidepressant, antiallergic, anti-inflammatory, antidiarrheal, analgesic, regulating gastrointestinal function and reducing visceral sensitivity, and improving sleep. It is safe and has few side effects, and can be administered to the patient over a long term for conditioning treatment of IBS.

Albiflorin is a monoterpenoid compound, with the molecular formula of $C_{23}H_{28}O_{11}$ and the molecular weight of 480.46. The molecular structure thereof is shown as Formula (I). It is a natural active substance derived from the roots of *Paeonia lactiflora* Pall, *Paeonia veitchii* Lynch and *P. suffrsticosa* Andrz of Ranuculaceae plants.

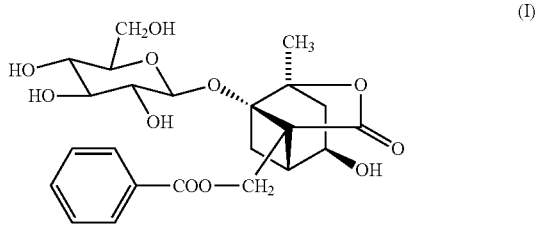

(I)

Albiflorin has a cyclic structure of lactone, but without a hemiacetal structure. It is converted under anaerobic condition into two products, paeonilactone A and paeonilactone B, respectively. The structures of paeonilactone A and B are shown as Formula (II) and Formula (III), respectively:

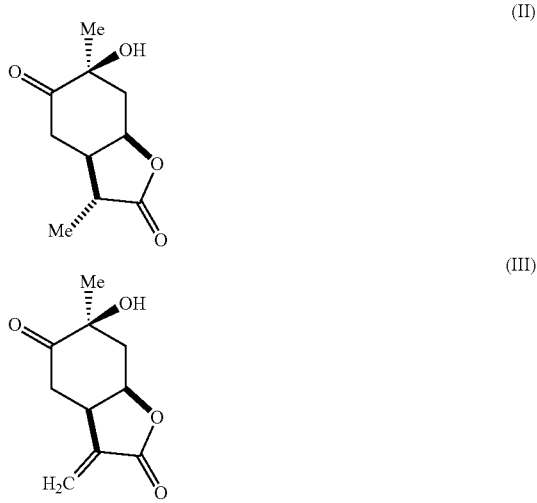

Modern pharmacological studies indicate that, albiflorin has analgesic, sedative and anticonvulsant effects, immune system-related effect, smooth muscle-related effect, anti-inflammatory effect, effect against pathogenic microorganisms, and liver protection effect. Clinically speaking, it is mainly used for anti-epilepsia, analgesia, drug abuse rehabilitation, nausea-stopping, the treatment of rheumatoid arthritis, the treatment of bacillary dysentery and enteritis, the treatment of viral hepatitis, the treatment of age-related diseases, the resistance to barium sulfate flocculation and mucus dissolution. The use of albiflorin for the prevention and treatment of irritable bowel syndrome has not yet been reported.

SUMMARY OF THE INVENTION

A object of the present invention is to provide a use of albiflorin or a pharmaceutically acceptable salt thereof in the preparation of a medicament or a health-care food for preventing, relieving and/or treating irritable bowel syndrome, particularly diarrhea-predominant irritable bowel syndrome, and more particularly preventing and treating diarrhea-predominant irritable bowel syndrome related to depression and/or anxiety.

In an embodiment, the purity of albiflorin or a pharmaceutically acceptable salt thereof is 50%-100%, preferably 80%-100%, and more preferably 90%-100%.

In another embodiment, the medicament consists of albiflorin or a pharmaceutically acceptable salt thereof and a pharmaceutically acceptable carrier.

Using methods of the prior art, the medicament could be formulated as a tablet, a capsule, a pill, a powder, a granule, a syrup, a solution, an emulsion, an injection, a spray, an aerosol, or a patch.

Another object of the present invention is to provide a medicament or a health-care food for preventing, relieving and/or treating irritable bowel syndrome, characterized in that the medicament or the health-care food comprises at least one of the following substances: albiflorin or a pharmaceutically acceptable salt thereof, a metabolite of albiflorin, a solvate of albiflorin, a herb extract comprising albiflorin or a herb comprising albiflorin. In particular, the present invention provides a medicament or a health-care food for preventing, relieving and/or treating irritable bowel syndrome, characterized in that the medicament or the health-care food comprises one of the following substances: albiflorin or a pharmaceutically acceptable salt thereof, a metabolite of albiflorin, a solvate of albiflorin, a herb extract comprising albiflorin as the main active ingredient or a herb comprising albiflorin as the main active ingredient.

In an embodiment, the irritable bowel syndrome is diarrhea-predominant irritable bowel syndrome, in particular diarrhea-predominant irritable bowel syndrome related to depression and/or anxiety.

In another embodiment, the content of albiflorin in the herb extract comprising albiflorin is 6%-99%, preferably 6%-50%, more preferably 10%-40%, and most preferably 15%-25%.

In another embodiment, the solvate of albiflorin is a hydrate of albiflorin.

In another embodiment, the herb comprising albiflorin is selected from the group consisting of *Paeonia lactiflora* Pall and *P. suffrsticosa* Andrz.

In another embodiment, the metabolite of albiflorin is selected from the group consisting of paeonilactone A and paeonilactone B.

Another object of the present invention is to provide a method for preventing, relieving and/or treating irritable bowel syndrome, comprising administering to the patient in need thereof a therapeutically effective amount of one of the following substances: albiflorin or a pharmaceutically acceptable salt thereof, a metabolite of albiflorin, a solvate of albiflorin, a herb extract comprising albiflorin or a herb comprising albiflorin.

In an embodiment, the irritable bowel syndrome is diarrhea-predominant irritable bowel syndrome, in particular diarrhea-predominant irritable bowel syndrome related to depression and/or anxiety.

In another embodiment, the content of albiflorin in the herb extract comprising albiflorin is 6%-99%.

In another embodiment, the solvate of albiflorin is a hydrate of albiflorin.

In another embodiment, the herb comprising albiflorin is selected from the group consisting of *Paeonia lactiflora* Pall and *P. suffrsticosa* Andrz.

In another embodiment, the metabolite of albiflorin is selected from the group consisting of paeonilactone A and paeonilactone B.

In other words, the object of the present invention is to provide albiflorin or a pharmaceutically acceptable salt thereof, a metabolite of albiflorin, a solvate of albiflorin, a herb extract comprising albiflorin or a herb comprising albiflorin, which have efficacy of preventing, relieving and treating diarrhea-predominant irritable bowel syndrome related to depression and/or anxiety. As for the existing problems in the prior art, the present invention provides a novel medicinal use and health-care use of albiflorin or a pharmaceutically acceptable salt thereof or a solvate thereof, a metabolite of albiflorin, a peony extract comprising albiflorin or a herb comprising albiflorin, i.e. a novel use in a medicament or a health-care food for preventing, relieving and treating irritable bowel syndrome.

Health-care food, also called as dietary supplement, is an oral product or preparation containing nutrients, which are taken for the purpose of increasing the nutrient in addition to daily meals. It is not a drug, but a kind of food, whereas it also differs from those on the table during three meals a day. "Health-care food" falls into the scope of food, but differs from that in the traditional sense. Its function is intended to supply nutrients in addition to daily meals, regulate body functions, and enhance physical fitness.

In order to achieve the above objects, the present invention provides a use of albiflorin or a pharmaceutically acceptable salt thereof in the preparation of a medicament or a health-care food for preventing, relieving and/or treating irritable bowel syndrome, in particular preventing and treating diarrhea-predominant irritable bowel syndrome related to depression and/or anxiety.

During the screening of natural active ingredients useful for preventing and treating irritable bowel syndrome, the inventor found that albiflorin or a pharmaceutically acceptable salt thereof, which is one of the chemical components presented in the extract of traditional Chinese medicine peony, possesses a significant efficacy, and found that the two metabolites of albiflorin in human body, paeonilactone A and paeonilactone B, also have medicinal value in treating and preventing irritable bowel syndrome.

The term "albiflorin" used herein refers to the racemates, stereoisomers, or mixtures of stereoisomers mixed in any proportion of albiflorin.

The term "pharmaceutically acceptable salt of albiflorin" used herein is a physiologically acceptable salt of albiflorin, especially when being administered to humans and/or mammals as a medicament. In particular, the salt includes an addition salt obtained from the reaction between albiflorin and an acid; the acid is selected from the group consisting of one or more of hydrochloric acid, fumaric acid, maleic acid, citric acid and succinic acid, all these acids mentioned are used for the purpose of illustration only, and thus are not limitative of the scope of the present invention.

In an embodiment, the medicament consists of albiflorin or a pharmaceutically acceptable salt thereof and a pharmaceutically acceptable carrier.

In particular, the pharmaceutically acceptable carrier is generally recognized by the authorities in the field of medicament and health-care food to be used for this purpose and used as inactive ingredient of medicament. The summary of pharmaceutically acceptable carriers can be found in "Handbook of pharmaceutical excipients" (2nd edition, edited by A. Wade and P. J. Weller; published by the American Pharmaceutical Association, Washington and The Pharmaceutical Press, London, 1994) and other reference books.

Especially, the carrier includes a excipient such as starch, water, and the like; a lubricant such as magnesium stearate, and the like; a disintegrant such as microcrystalline cellulose, and the like; a filler such as lactose, and the like; a binder, such as pregelatinized starch, dextrin, and the like; a sweetener; an antioxidant; a preservative; a flavoring agent; a fragrance; and the like.

In another embodiment, the medicament is presented in the form of a tablet, a capsule, a pill, a powder, a granule, a syrup, a solution, an injection, a spray, an aerosol, or a patch.

In another embodiment, the medicament is administered via gastrointestinal route and parenteral route.

In particular, the route of parenteral administration is selected from the group consisting of injection administration, respiratory tract administration, transdermal administration, mucosal administration and cavity administration.

More particularly, the formulation for parenteral administration is selected from the group consisting of an injection, a spray, an aerosol, and a patch, and the like.

In particular, the formulation for gastrointestinal administration is selected from the group consisting of a tablet, a capsule, a powder, a granule, a pill, a solution, and a syrup and the like.

In another embodiment, the purity of albiflorin or a pharmaceutically acceptable salt thereof is 50%-100%, preferably 80%-100%, and more preferably 90%-100%.

In another aspect, the present invention provides a use of a solvate of albiflorin in the preparation of a medicament or a health-care food for preventing, relieving and/or treating irritable bowel syndrome.

In another embodiment, the solvate of albiflorin is a hydrate of albiflorin. The present invention also provides a use of a herb comprising albiflorin or a herb extract comprising albiflorin in the preparation of a medicament or a health-care food for preventing, relieving and/or treating irritable bowel syndrome, in particular preventing, relieving and/or treating diarrhea-predominant irritable bowel syndrome related to depression and/or anxiety.

Wherein, the herb comprising albiflorin is selected from the group consisting of the herb peony or *Paeonia* suffrsticosa Andrz, preferably *Paeonia lactiflora* Pall; the content of albiflorin in the herb extract comprising albiflorin is ≥6%.

In particular, the content of albiflorin in the herb extract comprising albiflorin is 6%-99%, preferably 6%-50%, more preferably 10%-40%, and most preferably 15%-25%.

The present invention also provides a use of a metabolite of albiflorin in the preparation of a medicament or a health-care food for preventing, relieving and/or treating irritable bowel syndrome.

Wherein, the metabolite of albiflorin is paeonilactone A or paeonilactone B.

In still another aspect, the present invention provides a medicament for preventing, relieving and/or treating irritable bowel syndrome, comprising albiflorin or a pharmaceutically acceptable salt thereof.

Wherein, the purity of albiflorin or a pharmaceutically acceptable salt thereof is 50%-100%, preferably 80%-100%, and more preferably 90%-100%.

Wherein, the medicament also comprises a pharmaceutically acceptable carrier.

In particular, the pharmaceutically acceptable salt of albiflorin is a physiologically acceptable salt of albiflorin, especially when being administered to humans and/or mammals as a medicament.

Wherein, the salt includes an addition salt obtained from the reaction between albiflorin and an acid.

In particular, the acid is selected from the group consisting of one or more of hydrochloric acid, fumaric acid, maleic acid, citric acid and succinic acid, all these acids mentioned are used for the purpose of illustration only, and thus are not limitative of the scope of the present invention.

In still another aspect, the present invention provides a medicament for preventing, relieving and/or treating irritable bowel syndrome, comprising at least one of the following substances: a metabolite of albiflorin, a solvate of albiflorin, a herb comprising albiflorin or a herb extract comprising albiflorin.

Wherein, the medicament consists of one of a metabolite of albiflorin, a composition of albiflorin, a herb comprising albiflorin or a herb extract comprising albiflorin, and a pharmaceutically acceptable carrier.

In particular, the content of albiflorin in the herb extract comprising albiflorin is ≥6%.

Especially, the content of albiflorin in the herb extract comprising albiflorin is 6%-99%, preferably 6%-50%, more preferably 10%-40%, and most preferably 15%-25%.

Wherein, the metabolite of albiflorin is paeonilactone A or paeonilactone B.

In an embodiment, the solvate of albiflorin is a hydrate of albiflorin.

In another embodiment, the herb comprising albiflorin is selected from the group consisting of peony and *Paeonia suffrsticosa* Andrz, preferably *Paeonia lactiflora* Pall.

In particular, the carrier includes a excipient such as starch, water, and the like; a lubricant such as magnesium stearate, and the like; a disintegrant such as microcrystalline cellulose, and the like; a filler such as lactose, and the like; a binder, such as pregelatinized starch, dextrin, and the like; a sweetener; an antioxidant; a preservative; a flavoring agent; a fragrance; and the like.

Using methods known in the art, the medicament could be formulated into various dosage forms, such as a tablet, a capsule, a pill, a powder, a granule, a syrup, a solution, an emulsion, an injection, a spray, an aerosol, or a patch and the like.

In still another aspect, the present invention provides a health-care food for preventing, relieving and/or treating irritable bowel syndrome, comprising one of the following substances: albiflorin or a pharmaceutically acceptable salt thereof, a metabolite of albiflorin, a solvate of albiflorin, a herb extract comprising albiflorin or a herb comprising albiflorin.

Wherein, the purity of albiflorin is 50%-100%, preferably 80%-100%, and more preferably 90%-100%.

In particular, the content of albiflorin in the herb extract comprising albiflorin is 6%-99%, preferably 6%-50%, more preferably 10%-40%, and most preferably 15%-25%.

The present invention also provides a method for treating irritable bowel syndrome, comprising administering to the subject in need thereof a therapeutically effective amount of a pharmaceutical composition of albiflorin. The therapeutically effective amount is 0.2-1.8 mg/kg·d, preferably 0.35-1.5 mg/kg·d, further preferably 0.5-1.2 mg/kg·d.

Unless otherwise indicated, the term "therapeutically effective amount" as used herein refers to the amount of medicament intended for having desirable effect; "therapeutically effective amount" can be modified and changed, and finally determined by medical staff, and the factors which should be taken into consideration include the administration routes and formulation properties; body weights, ages and other general conditions of subjects, as well as the natures and severity of the diseases to be treated.

The present invention has the following values and advantages:

1. The present invention explores the new medicinal value of known compound albiflorin or a pharmaceutically acceptable salt thereof or a solvate thereof, which can be applied for the prevention and treatment of irritable bowel syndrome, and prepared into a medicament or a health-care food for preventing, relieving and/or treating irritable bowel syndrome, and thereby opening up a new field for the application of the herb *Paeonia lactiflora* Pall and the like.

2. A series of experimental studies of the present invention demonstrates that, albiflorin or a pharmaceutically acceptable salt thereof has significant effect on the prevention and treatment of irritable bowel syndrome, and is the main active ingredient of peony, peony extract for preventing, relieving and/or treating irritable bowel syndrome.

3. The present invention explores in-depth that, albiflorin or a pharmaceutically acceptable salt thereof has multiple functions of antidepressant, antianxiety, antiallergic, anti-inflammatory, analgesic, regulating gastrointestinal function and improving sleep at the same time. It is safe and has few side effects. It is useful in developing a medicament or a health-care food for preventing, relieving and/or treating irritable bowel syndrome, and has a high druggability and wide use.

4. The product of the present invention has sufficient and low-cost sources of raw materials, high clinical safety, simple preparing process and high controllable quality. It could be formulated into various dosage forms, administered in a small dose, easily applied, and thus readily promoted. It can also reduce the medical cost.

5. According to the present invention, albiflorin or a pharmaceutically acceptable salt thereof as a single active ingredient can be prepared into a medicament for preventing, relieving and/or treating irritable bowel syndrome, alternatively, albiflorin or a pharmaceutically acceptable salt thereof can be prepared into a combinatorial medicament for preventing, relieving and/or treating irritable bowel syndrome, in combination with other ingredients (for example, paeoniflorin, hesperidin, menthol, and the like).

DESCRIPTION OF THE DRAWINGS

FIG. 1 is a flow chart of chronic stress process of rat.

DETAILED DESCRIPTION OF THE INVENTION

The present invention will now be further described by reference to the following examples. These examples are for illustrative purposes only, and thus not to be construed as a limitation of the scope of the present invention. In the following examples, the experimental methods without specifically indicated conditions are often corresponded with conventional conditions, or corresponded with the conditions recommended by the manufacturers.

The beneficial effects of medicaments of the present invention will be further described by means of the following experimental examples, these experimental examples include the pharmacodynamic tests of the medicaments of the present invention.

Example 1

100 g of albiflorin with a purity of 96.77% was added to 50 g of starch and 10 g of starch silica, mixed well and then directly filled into hard gelatin capsules, to obtain the capsules comprising 40 mg of albiflorin per capsule.

Example 2

100 g of albiflorin with a purity of 92% was ground and sifted through a 100 mesh sieve, and then mixed well with 100 g of starch which was sifted through a 100 mesh sieve. An appropriate amount of starch slurry was added under homogeneous stir, the mixture was sifted through a 16 mesh iron wire sieve, dried below 60° C., and then granulated. An appropriate amount of magnesium stearate was added, the mixture was mixed well and placed into a tablet press to obtain the tablets comprising 30 mg of albiflorin per tablet.

Example 3

10 g of albiflorin with a purity of 98.5% and 90 g of sodium chloride was added to water for injection and dissolved under stirring. After adding water for injection up to 1000 ml, the solution was then filtered with 0.22 μm microporous membrane, subdivided and sealed, and sterilized to obtain an infusion formulation of albiflorin and sodium chloride.

Example 4

100 g of the extract of *Paeonia lactiflora* Pall with an albiflorin content of 13% was ground to 200 mesh, added into 100 g of swollen sodium carboxymethyl cellulose (CMC), and homogeneously stirred. Distilled water was added until the volume reaches 10 L, the mixture was stirred to obtain a suspension.

Example 5: Test of Albiflorin and Paeoniflorin for Treating Diarrhea of Irritable Bowel Syndrome Induced by Restraint Stress in Rat The restraint stress stimulus method was used to induce abnormal defecation in rats, thereby leading to increase of colon smooth muscle movement and accelerating intestinal transport. The test of albiflorin and paeoniflorin for treating the diarrhea model of irritable bowel syndrome induced by restraint stress in rats was carried out to verify the improved effect of drug dosage on the grade of loose stool and the number of loose stool.

5.1 Materials
5.1.1 Animals 60 healthy SD rats (half male and half female), supplied by the Animal Department, Capital Medical University. The weight of each rat is between 200 g and 230 g. The rats were fed in separate cages in a room with day and night light changes for one week, the room temperature is between 20° C. and 22° C., and the rats had free access to water and food.

5.1.2 Drugs

The positive drugs: loperamide hydrochloride (Imodium™), supplied by Xi'an Janssen Pharmaceutical Co., Ltd.; trimebutine maleate (Yuanshengliwei™), supplied by Kaikai Yuansheng Pharmaceutical Co., Ltd.

The test drugs: albiflorin (≥98%), supplied by Beijing Wonner Biotech Co., Ltd.; paeoniflorin (≥98%), supplied by Beijing Wonner Biotech Co., Ltd.

5.2 Methods

The animals were randomly divided into 10 groups as follows: normal control group; model control group (normal saline); high-, mid- and low-dose groups of test drugs (albiflorin and paeoniflorin); and positive control groups (loperamide hydrochloride (Imodium™) and trimebutine maleate (Yuanshengliwei™)). Gavage administration was performed on each group once a day, for 7 consecutive days.

The rats were deprived of food for 24 hours before the test. Half an hour after the last administration, the rats were anesthetized with ethyl ether. After the rat fainted away, its front shoulder, front upper limbs and chest were bound with scotch tape to prevent the front upper limbs from scratching its face, but the movement of the front upper limbs was not limited. A glass ball with a diameter of 3 mm was placed into the rectum 3 cm away from anus. The rats were moved rapidly into cages which were padded with clean filter paper. Timing started when the rat woke up, and the binding time was one hour. The number of fecal pellets excreted by the rat in one hour and the time for excreting glass ball were recorded. Statistical analysis of data was performed using t-test for intergroup comparison.

5.3 Experimental Results

TABLE 1

Test results of treating diarrhea of irritable bowel syndrome in rat

| Groups | Number of animals | Number of fecal pellets excreted in 1 h | Time for excreting glass ball (min) |
| --- | --- | --- | --- |
| Normal control group | 10 | 2.10 ± 2.8 | 31.00 ± 26.13 |
| Model control group | 10 | 4.20 ± 2.04$^{\Delta}$ | 10.40 ± 10.12 |
| Loperamide hydrochloride, 0.17 mg/kg/d | 10 | 1.40 ± 0.97** | 26.00 ± 28.30 |
| Trimebutine maleate, 6.25 mg/kg/d | 10 | 3.70 ± 2.26 | 17.80 ± 21.88 |
| Albiflorin, high-dose, 9.8 mg/kg/d | 10 | 2.50 ± 1.27* | 10.60 ± 17.58 |
| Albiflorin, mid-dose, 4.9 mg/kg/d | 10 | 1.80 ± 1.48** | 12.00 ± 17.53 |
| Albiflorin, low-dose, 2.45 mg/kg/d | 10 | 2.60 ± 1.84* | 19.90 ± 17.69 |
| Paeoniflorin, high-dose, 9.8 mg/kg/d | 10 | 3.71 ± 2.02 | 10.70 ± 16.06 |
| Paeoniflorin, mid-dose, 4.9 mg/kg/d | 10 | 3.96 ± 1.36 | 10.50 ± 14.03 |
| Paeoniflorin, low-dose, 2.45 mg/kg/d | 10 | 4.10 ± 1.81 | 10.64 ± 15.01 |

Half an hour after the test drugs were administrated, when the glass ball was placed into the rectum 3 cm away from anus, the time for excreting glass ball and the number of fecal pellets excreted by the rat in one hour were recorded.
$^{\Delta}$compared with normal control group, $p < 0.05$;
$^{\Delta\Delta}$ compared with normal control group, $p < 0.01$;
*compared with model control group, $p < 0.05$;
**compared with model control group, $p < 0.01$.

5.4 Conclusions

It can be seen from the test results of albiflorin and paeoniflorin for treating diarrhea of irritable bowel syndrome in animals that, the number of fecal pellets excreted in high-, mid- and low-dose groups of albiflorin was decreased obviously ($p<0.05$, $p<0.01$); whereas there was only a trend to decrease the number of fecal pellets in high-, mid- and low-dose groups of paeoniflorin ($p>0.05$). Therefore, albiflorin is the main active ingredient of total glucosides of *Paeonia lactiflora* Pall for treating diarrhea and abdominal pain.

Example 6: Test of Albiflorin and Paeoniflorin for Treating Abdominal Pain of Irritable Bowel Syndrome in Mice

6.1 Materials 6.1.1 Animals

70 ICR mice (half male and half female), supplied by the Animal Department, Capital Medical University. The weight of each mouse is between 20 g and 22 g.

6.1.2 Drugs

The positive drugs: pinaverium bromide tablets (Dicetel™), supplied by Solvay Pharma, Germany; loperamide hydrochloride (Imodium™), supplied by Xi'an Janssen Pharmaceutical Co., Ltd.

The test drugs: albiflorin (≥98%), supplied by Beijing Wonner Biotech Co., Ltd.; paeoniflorin (≥98%), supplied by Beijing Wonner Biotech Co., Ltd.

6.2 Methods 6.2.1 Modeling

Neostigmine™ was administered to the mice by subcutaneous injection (0.1 ml/20 g body weight). 1 ml of the injection contains 0.03 mg of Neostigmine™.

6.2.2 Methods and Administration

The mice were randomly divided into 10 groups as follows: normal control group (negative control group); pathology modeling control group; high-, mid- and low-dose groups of test drugs albiflorin; high-, mid- and low-dose groups of paeoniflorin; and positive control groups (pinaverium bromide tablets (Dicetel™) and loperamide hydrochloride (Imodium™)).

All the animals were deprived of food for 12 hours before the test. Gavage administration of distilled water (0.4 ml/20 g) was performed on normal control group and pathology modeling control group, and gavage administration of drugs (0.4 ml/20 g) was performed respectively on groups of test drugs and positive control groups (pinaverium bromide and loperamide hydrochloride). The gavage administration lasted for 7 consecutive days. 30 minutes after the last administration, normal saline (0.1 ml/20 g body weight) was injected subcutaneously into the mice of normal control group, and Neostigmine™ was injected according to the modeling method into the mice of other groups to induce small intestine spasm models. After 15 minutes, gavage administration of carbon powder paste was performed on all groups (0.2 ml/10 g body weight, each dosage contains 0.05 g of carbon powder and 0.02 g of carboxymethyl cellulose). The animals were killed 20 minutes later. The propulsive length of carbon powder in small intestine and the total length of small intestine were measured respectively, and then the propulsive rate of carbon powder was calculated. Statistical analysis of data was performed using t-test for intergroup comparison.

The propulsive distance: to measure the propulsive length of carbon powder in small intestine.

Propulsive rate (%)=(propulsive length/total length of small intestine)×100%.

6.3 Results

The results are shown in Table 2.

TABLE 2

Test results of treating abdominal pain of irritable bowel syndrome in mice

| Groups | Number of animals | Propulsive distance (cm) | Propulsive rate (%) |
| --- | --- | --- | --- |
| Normal control group | 10 | 23.90 ± 5.36 | 53.56 ± 12.30 |
| Pathology modeling control group | 10 | 33.25 ± 4.97[ΔΔ] | 74.49 ± 7.14[ΔΔ] |
| Loperamide hydrochloride group, 2.4 mg/kg/d | 10 | 22.00 ± 4.42** | 59.63 ± 11.25 |
| Pinaverium bromide group, 45.05 mg/kg/d | 10 | 21.40 ± 2.32** | 57.87 ± 6.76** |
| Albiflorin, high-dose, 14 mg/kg/d | 10 | 22.80 ± 4.78** | 57.47 ± 10.67** |
| Albiflorin, mid-dose, 7 mg/kg/d | 10 | 20.80 ± 4.64** | 54.53 ± 9.39** |
| Albiflorin, low-dose, 3.5 mg/kg/d | 10 | 22.10 ± 3.90** | 57.05 ± 4.69** |
| Paeoniflorin, high-dose, 14 mg/kg/d | 10 | 28.80 ± 3.79* | 65.64 ± 8.80 |
| Paeoniflorin, mid-dose, 7 mg/kg/d | 10 | 31.00 ± 1.93 | 71.92 ± 7.51 |
| Paeoniflorin, low-dose, 3.5 mg/kg/d | 10 | 31.80 ± 3.79 | 72.64 ± 4.69 |

[Δ] compared with normal control group, $p < 0.05$;
[ΔΔ] compared with normal control group, $p < 0.01$;
*compared with pathology modeling control group, $p < 0.05$;
**compared with pathology modeling control group, $p < 0.01$.

6.4 Conclusions

It can be seen from the test results of abdominal pain of irritable bowel syndrome in mice that, the propulsive distance and the propulsive rate of carbon powder suspension in mice intestine tract stimulated by Neostigmine™ were decreased obviously in high-, mid- and low-dose groups of albiflorin ($p<0.01$), the efficacy of albiflorin was comparable to that of positive drugs loperamide hydrochloride and pinaverium bromide; whereas the propulsive distance and the propulsive rate of carbon powder suspension in mice intestine tract stimulated by Neostigmine™ were decreased only in high-dose group of paeoniflorin (p<0.05). The results demonstrated that, albiflorin can obviously relieve or treat abdominal pain of mice, and albiflorin is the main active ingredient of total glucosides of *Paeonia lactiflora* Pall for treating irritable bowel syndrome.

Example 7: Test of Albiflorin in Mice on Sleep Induced by Subthreshold Dose of Pentobarbital Sodium 7.1 Materials Animals: ICR mice of SPF level, 18-22 g, supplied by the Experimental Animal Department, Peking University Health Science Center.

Instrument: a stopwatch and the like.

Drugs and reagents: albiflorin (98%, supplied by Beijing Wonner Biotech Co., Ltd.), diazepam (supplied by Harbin Pharmaceutical Group, Sixth Pharm Factory), pentobarbital sodium (supplied by Merck Co.).

7.2 Methods

Mice with a body weight of 18-22 g, male and female, were selected. Mice with a single-sex were used in each test. The mice were randomly divided into groups as follows: albiflorin group, diazepam group (positive control group) and control group (normal saline). There were 10 mice in each group. 60 minutes after the gavage administration, threshold dose of pentobarbital sodium (50 mg/kg) was injected intraperitoneally. The disappearance of righting reflex was recorded as time to fall asleep, and the period from the righting reflex being disappeared until the righting reflex being recovered was recorded as sleep duration time. Compared with the control group, the significance was determined by time t test.

7.3 Results

Albiflorin and diazepam can obviously prolong the sleep time of mice induced by threshold dose of pentobarbital sodium, indicating that there is a synergy between albiflorin and pentobarbital sodium, and albiflorin has a hypnotic effect. The results are shown in Table 3.

TABLE 3

Effect of albiflorin in mice on the sleep time induced by threshold dose of pentobarbital sodium ($x \pm s$, n = 10)

| Groups | Dose (mg/kg) | Sleep time (min) |
|---|---|---|
| Normal saline | | 72.8 ± 22.8 |
| Albiflorin | 14 | 98.8 ± 12.4** |
| Albiflorin | 7 | 90.2 ± 15.1* |
| Diazepam | 1 | 102.0 ± 16.2** |
| Diazepam | 0.5 | 96. ± 14.6** |

Compared with normal saline group:
*p < 0.05
**p < 0.01

7.4 Conclusions

Albiflorin and positive drug diazepam all had synergy with pentobarbital sodium on increasing sleep time.

Example 8: Effect of Albiflorin in Mice in Light-Dark Shuttle Box Test (Anti-Anxiety Test)

8.1 Materials and Methods 8.1.1 Drugs

Albiflorin (96.77%), supplied by Beijing Wonner Biotech Co., Ltd.; Diazepam, produced by Jin-Hui Amino Acid Co., Ltd. (Tianjin, China).

8.1.2 Animals

KM mice, male, with body weight of 24-26 g, Class 2, supplied by the Experimental Animal Department, Peking University Health Science Center.

8.1.3 Instrument

Homemade shuttle light-dark box.

8.1.4 Methods 8.1.4.1 Grouping and Administration Methods of Animals:

Mice were randomly divided into 5 groups, i.e. high-dose group of albiflorin (14 mg/kg/d), mid-dose group of albiflorin (7 mg/kg/d), low-dose group of albiflorin (3.5 mg/kg/d), diazepam group (2.5 mg/kg/d), and normal control group. Gavage administration was performed once a day, for 7 consecutive days. During the administration, animals had free access to food and water. The test was carried out 1 hour after the administration on Day 8.

8.1.4.2 Light-Dark Box Tests in Mice:

Within the light-dark shuttle box (44 cm×21 cm×21 cm), the dark box accounts for one third thereof, with a cover on the top; and the light box accounts for two thirds thereof, with illumination brightness; and there is a hole between the two boxes for animal to pass through. During the test, mice were placed in the center of the light box, back to the dark box, and then observed. The number of times of entering into the dark box followed by returning to the light box in mice was counted, which was used as an index for the evaluation of anti-anxiety effect of a drug.

8.1.5 Statistical Analysis The data were expressed as $\bar{X} \pm SD$, and the experimental results were analyzed by one-way ANOVA, using SPSS 11.5 statistical software.

8.2 Results

Effect of albiflorin on the number of times of passing through box in mice in light-dark box test are shown in Table 4. All the high-, mid- and low-dose groups of albiflorin as well as diazepam group can significantly increase the number of times of returning from the dark box back to the light box in the mice, and have statistical significance in comparison to the normal control group.

TABLE 4

Effect of albiflorin on the number of times of passing through box in mice in the light-dark box test

| Groups | Number of animals | Dose (mg/kg/d) | Number of times of returning from dark box back to light box |
|---|---|---|---|
| Albiflorin, high-dose | 10 | 14 mg/kg/d | 13.9 ± 3.23** |
| Albiflorin, mid-dose | 10 | 7 mg/kg/d | 12.1 ± 3.51** |

TABLE 4-continued

Effect of albiflorin on the number of times of passing through box in mice in the light-dark box test

| Groups | Number of animals | Dose (mg/kg/d) | Number of times of returning from dark box back to light box |
|---|---|---|---|
| Albiflorin, low-dose | 10 | 3.5 mg/kg/d | 10.6 ± 3.42* |
| Diazepam | 10 | 2.5 mg/kg/d | 13.6 ± 3.35** |
| Normal control group | 10 | — | 6.9 ± 3.74 |

Note:
*p < 0.05,
**p < 0.01, compared with the normal control group.

8.3 Conclusions

The light-dark box test is an experimental model for anti-anxiety study, which is designed on the basis of congenital aversion to hard light and spontaneous exploratory behavior in new environment of murine. The drugs having anti-anxiety effect (such as diazepam and the like) can increase the speed of passing through box and the residence time in light box of animal, whereas non anti-anxiety agents do not have such an effect. The results of light-dark box test of the present test showed that all the high-, mid- and low-dose groups of albiflorin as well as diazepam group can significantly increase the number of times of returning from the dark box back to the light box in mice, and have statistical significance in comparison to normal control group. The experimental results showed that albiflorin had certain anti-anxiety effect.

Example 9: Test of Effect of Albiflorin on Chronic Stress Depression Model in Rats 9.1 Materials
9.1.1 Animals
Rats:
Species and strain: Wistar SPF level
Origin: Sibeifu Experiment Animal Technology Co., Ltd. (Beijing)
License number: SOCK (Beijing) 2011-0004
Initial body weight: 140-160 g
Sex: male
9.1.2 Drugs and Reagents
Albiflorin, supplied by Beijing Wonner Biotech Co., Ltd., batch number: 110522, content or purity: ≥98%, solvent: distilled water.
Fluoxetine, produced by Changzhou No. 4 Pharmaceutical Factory, content: ≥99%, solvent: distilled water.
9.2 Experimental Methods
9.2.1 Experimental Procedure of Chronic Stress Model in Rats After purchasing, the rats were fed for 3 days to adapt to the environment. At first, a sucrose aqueous solution-drinking training was performed for 48 h, then a sugar aqueous solution baseline test was carried out after the training. The rats were divided randomly and evenly into groups according to sucrose preference. Then, a chronic unpredictable stress (CUS) process was performed for about 5 weeks, and distilled water, fluoxetine and albiflorin were continuously administered once a day respectively to intervene. After the end of the chronic stress, an ethology test, comprising: 1) a sucrose aqueous solution-drinking test; and 2) an open field test, was carried out. The experimental procedure is shown in FIG. 1.

9.2.2 Administration Process of Chronic Stress Model in Rats

The rats were divided randomly and evenly into 6 groups according to sucrose preference as follows: blank control group (Con), model group (CUS), positive control fluoxetine group (Flx)(10 mg/kg), three doses of albiflorin groups (3.5 mg/kg, 7.0 mg/kg, 14.0 mg/kg). All drugs were formulated with distilled water.

The gavage administration was carried out at 8 o'clock every morning, once a day, for 38 consecutive days. The sucrose aqueous solution-drinking test was performed on Day 39, and the open field test was performed on Day 41.

9.2.3 Establishment of Chronic Stress Model in Rats

Since the body will readily produce tolerance to the stimulation of a single stressor, the present test used multiple unpredictable stress methods, which were performed alternately, to establish the chronic unpredictable stress model in rats. The total duration of chronic stress was 5 w, the stress methods were as follows: ① food deprivation (fasting) for 24 h; ② water deprivation for 24 h; ③ overnight illumination; ④ soiled cage (200 ml of water was add to 150 g of padding); ⑤ stroboscopic+white noise for 2 h; ⑥ force swimming (water temperature was 10° C.) for 5 min; ⑦ cage tilt (tilt for 45°) for 24 h; ⑧ tail pinch (pinch the tail at 1 cm away from the tail end) for 5 min; ⑨ restraint for 2 h. One of the above stress methods was randomly selected and used on each day, but the water deprivation and food deprivation were not used successively. The corresponding drugs were administered 1 hour before stress on each morning.

9.2.4 Ethology Tests
9.2.4.1 Sucrose Aqueous Solution-Drinking Test

After purchasing, the rats were fed for 3 days to adapt to the environment. Then, a sucrose aqueous solution-drinking training was performed for 48 h, which comprised the steps of: depriving of food and water, providing only a 1% sucrose aqueous solution on the first 24 h, and providing a 1% sucrose aqueous solution and tap water simultaneously on the last 24 h to train the rats. After the training, the rats were fed with routine food and water for 3 days, and the sucrose aqueous solution-drinking baseline test was carried out, which comprised the steps of: depriving of food and water for 14 h, then allowing the rats to drink two different bottles of water freely, wherein one bottle contained 1% sucrose aqueous solution, the other one contained tap water. The drinking amounts (g) of two bottles of water in 1 h were measured respectively to calculate sucrose preference. Sucrose preference (%)=drinking amount of sucrose aqueous solution/(drinking amount of sucrose aqueous solution+drinking amount of tap water)×100%. After the end of the stress procedure, the sucrose aqueous solution-drinking test was performed again according to the same method to calculate sucrose preference.

9.2.4.2 Open Field Test in Rats

On Day 3 after the end of the stress procedure, a square open field box (76 cm×76 cm×46 cm) was used, the bottom of which was divided by black lines into 16 squares with equal area. The rat was placed in the middle square of the open field box, and a 60 W bulb was placed 45 cm above the middle square to illuminate the box. The movement of the rat within 5 min was observed, including: the number of times of horizontal crossing squares (the number of times that more than three paws crossed to the adjacent square), and the number of times of vertical standing (the number of times that two forelimbs left more than 1 cm away from the ground). Notes: the experimental test environment should be kept as quiet as possible; the rat should be placed in the same location and the same direction each time; the excreta of the animals should be cleaned after each test.

9.3 Data Processing and Statistical Methods

Experimental data were expressed as means±standard error (Means±SEM). The statistical analysis was carried out by one-way ANOVA, and the intergroup difference was determined by Bonferroni's test. The statistical software was GraphPad Prism.5.0.

the number of times of horizontal movement of rats in open field was obviously increased after long-term gavage administration of fluoxetine (10 mg/kg). 3.5 mg/kg of albiflorin also obviously increased the number of times of horizontal movement of rats in open field. Although 7.0 mg/kg and 14.0 mg/kg of albiflorin can not obviously increase the number of times of horizontal movement of rats in open field, there was a trend of increase.

9.4.2.2 Effect of Chronic Administration of Albiflorin on the Number of Times of Vertical Movement of Rats in Open Field Compared with the blank group, the number of times of vertical movement of rats in open field was obviously decreased in chronic stress model group, indicating that the modeling was succeeded. Compared with the model group, the number of times of vertical movement of rats in open field was obviously increased after long-term gavage administration of fluoxetine (10 mg/kg). 3.5-14.0 mg/kg of albiflorin also obviously increased the number of times of vertical movement of rats in open field.

The results are shown in Table 5.

TABLE 5

Effect of albiflorin on sugar aqueous solution preference and open movement test in chronic stress rats

| Groups | Sugar aqueous solution preference (%) | Number of times of horizontal movement in open field | Number of times of vertical movement in open field |
| --- | --- | --- | --- |
| Con | 85.80 ± 8.18 | 86.4 ± 8.02 | 27.60 ± 2.70 |
| CUS | 39.55 ± 10.74** | 58.10 ± 7.52* | 12.30 ± 1.75*** |
| Flx | 70.63 ± 6.86# | 90.60 ± 7.72# | 20.80 ± 1.93# |
| Albiflorin, 3.5 mg/kg | 60.04 ± 10.86 | 95.40 ± 9.23# | 20.50 ± 1.81# |
| Albiflorin, 7.0 mg/kg | 76.19 ± 5.35## | 98.20 ± 8.61## | 21.10 ± 2.17# |
| Albiflorin, 14.0 mg/kg | 78.12 ± 4.04## | 104.10 ± 11.11## | 22.10 ± 2.66## |

*$p < 0.05$,
**$p < 0.01$,
***$p < 0.001$ vs. blank control group;
$p < 0.05$,
$p < 0.01$ vs. CUS 9.4 Experimental Results 9.4.1 Effect of Chronic Administration of Albiflorin on Sugar Aqueous Solution Preference in Rats Compared with the blank group, the sugar aqueous solution preference of rats in chronic stress model group was obviously decreased, indicating that the modeling was succeeded. Compared with the model group, the sugar aqueous solution preference of rats was obviously increased after long-term gavage administration of fluoxetine (10 mg/kg). 7.0 mg/kg and 14.0 mg/kg of albiflorin obviously increased the sugar aqueous solution preference of rats. Although 3.5 mg/kg of albiflorin did not obviously increase the sugar aqueous solution preference, there was a trend of increasing the sugar aqueous solution preference.

9.4.2 Effect of Chronic Administration of Albiflorin on Open Field Movement in Rats 9.4.2.1 Effect of Chronic Administration of Albiflorin on the Number of Times of Horizontal Movement of Rats in Open Field Compared with the blank group, the number of times of horizontal movement of rats in open field was obviously decreased in chronic stress model group, indicating that the modeling was succeeded. Compared with the model group, The results indicated that albiflorin had an anti-depression effect within the range of effective dose thereof in sucrose aqueous solution-drinking test. Albiflorin can obviously increase the number of times of open field movement in rats within the range of effective dose thereof, and showed an anti-depression effect in this model.

9.5 Conclusions

After chronic administration, albiflorin showed an anti-depression effect, and the effect of albiflorin was comparable to that of positive drug fluoxetine in sucrose aqueous solution-drinking model and open field model.

Example 10: Test of Extract of *Paeonia lactiflora* Pall for Treating Abdominal Pain of Irritable Bowel Syndrome in Mice 10.1 Materials 10.1.1 Animals 70 ICR mice (half male and half female), supplied by the Animal Department, Capital Medical University. The weight of each mouse is between 20 g and 22 g.

10.1.2 Drugs

The positive drugs: pinaverium bromide tablets (Dicetel™), supplied by Solvay Pharma, Germany; loperamide hydrochloride (Imodium™), supplied by Xi'an Janssen Pharmaceutical Co., Ltd.

The test drugs: extract of Paeonia lactiflora Pall (comprising 13% of albiflorin), supplied by Beijing Wonner Biotech Co., Ltd.

10.2 Methods 10.2.1 Modeling

Neostigmine™ was administered to the mice by subcutaneous injection (0.1 ml/20 g body weight). 1 ml of the injection contains 0.03 mg of Neostigmine™

10.2.2 Methods and Administration

The mice were randomly divided into 7 groups as follows: normal control group (negative control group); pathology modeling control group; high-, mid- and low-dose groups of test drug (extract of Paeonia lactiflora Pall); and positive control groups (pinaverium bromide tablets (Dicetel™) and loperamide hydrochloride (Imodium™)).

All the animals were deprived of food for 12 hours before the test. Gavage administration of distilled water (0.4 ml/20 g) was performed on normal control group and pathology modeling control group, and gavage administration of drugs (0.4 ml/20 g) was performed respectively on groups of test drugs and positive control groups (pinaverium bromide and loperamide hydrochloride). The gavage administration lasted for 7 consecutive days. 30 minutes after the last administration, normal saline (0.1 ml/20 g body weight) was injected subcutaneously into the mice of normal control group, and Neostigmine™ was injected according to the modeling method into the mice of other groups to induce small intestine spasm model. After 15 minutes, gavage administration of carbon powder paste was performed on all groups (0.2 ml/10 g body weight, each dosage contains 0.05 g of carbon powder and 0.02 g of carboxymethyl cellulose). The animals were killed 20 minutes later. The propulsive length of carbon powder in small intestine and the total length of small intestine were measured respectively, and then the propulsive rate of carbon powder was calculated.

Statistical analysis of data was performed using t-test for intergroup comparison.

The propulsive distance: to measure the propulsive length of carbon powder in small intestine.

Propulsive rate(%)=(propulsive length/total length of small intestine)×100%.

10.3 Results

The results are shown in Table 6.

TABLE 6

Test results of treating abdominal pain of irritable bowel syndrome in mice

| Groups | Number of animals | Propulsive distance (cm) | Propulsive rate (%) |
|---|---|---|---|
| Normal group | 10 | 22.87 ± 5.02 | 53.19 ± 12.13 |
| Pathology modeling control group | 10 | 34.25 ± 5.03** | 75.67 ± 6.89** |
| Loperamide hydrochloride group, 2.4 mg/kg/d | 10 | 22.35 ± 4.37$^{\Delta\Delta}$ | 58.98 ± 11.06 |
| Pinaverium bromide group, 45.05 mg/kg/d | 10 | 21.73 ± 2.40$^{\Delta\Delta}$ | 58.07 ± 6.50$^{\Delta\Delta}$ |
| Extract of Paeonia lactiflora Pall, high-dose, 100 mg/kg/d | 10 | 25.13 ± 4.52$^{\Delta\Delta}$ | 60.06 ± 10.19$^{\Delta}$ |
| Extract of Paeonia lactiflora Pall, mid-dose, 50 mg/kg/d | 10 | 21.32 ± 4.04$^{\Delta\Delta}$ | 53.81 ± 9.01$^{\Delta\Delta}$ |
| Extract of Paeonia lactiflora Pall, low-dose, 25 mg/kg/d | 10 | 23.41 ± 3.72$^{\Delta\Delta}$ | 56.75 ± 4.28$^{\Delta\Delta}$ |

* compared with normal control group, $p < 0.05$;
$^{\Delta}$compared with pathology modeling control group, $p < 0.05$;
$^{\Delta\Delta}$compared with pathology modeling control group, $p < 0.01$.

10.4 Conclusions

It can be seen from the results that, the extract of Paeonia lactiflora Pall can decrease the propulsive distance and the propulsive rate of carbon powder suspension in mice intestine tract stimulated by Neostigmine™. The high-, mid- and low-dose of extract of Paeonia lactiflora Pall can significantly decrease the propulsive distance ($p<0.01$), the efficacy of the extract of Paeonia lactiflora Pall was comparable to that of positive drugs loperamide hydrochloride and pinaverium bromide. The results demonstrated that, the extract of Paeonia lactiflora Pall had an efficacy of relieving or treating abdominal pain in mice.

What is claimed is:

1. A method for relieving and/or treating irritable bowel syndrome comprising administering to a subject in need thereof a medicament comprising albiflorin or a pharmaceutically acceptable salt thereof or a solvate thereof as the main active ingredient.

2. The method according to claim 1, wherein the irritable bowel syndrome is diarrhea-predominant irritable bowel syndrome.

3. The method according to claim 2, wherein the diarrhea-predominant irritable bowel syndrome is related to depression and/or anxiety.

4. The method according to claim 1 wherein the purity of albiflorin or a pharmaceutically acceptable salt thereof is 50%-100%.

5. The method according to claim 1, wherein the medicament consists of albiflorin or a pharmaceutically acceptable salt thereof and a pharmaceutically acceptable carrier.

6. The method according to claim 1, wherein the medicament is presented in the form of a tablet, a capsule, a pill, a powder, a granule, a syrup, a solution, an emulsion, an injection, a spray, an aerosol, or a patch.

7. The method according to claim 1, wherein the solvate of albiflorin is a hydrate of albiflorin.

* * * * *